US006516228B1

(12) United States Patent
Berrang et al.

(10) Patent No.: US 6,516,228 B1
(45) Date of Patent: Feb. 4, 2003

(54) IMPLANTABLE MICROPHONE FOR USE WITH A HEARING AID OR COCHLEAR PROSTHESIS

(75) Inventors: Peter G. Berrang, Victoria (CA); Stacey D. Jarvin, Brentwood Bay (CA); Alan J. Lupin, Victoria (CA); Sean A. McNiven, Victoria (CA)

(73) Assignee: Epic Biosonics Inc., Victoria (CA)

( * ) Notice: Subject to any disclaimer, the term of this patent is extended or adjusted under 35 U.S.C. 154(b) by 0 days.

(21) Appl. No.: 09/499,376

(22) Filed: Feb. 7, 2000

(51) Int. Cl.[7] .................................................. A61N 1/08
(52) U.S. Cl. ........................................................ 607/57
(58) Field of Search ................................ 181/130, 135; 381/174, 189, 191, 328; 600/23, 25; 607/2, 55, 56, 57

(56) References Cited

U.S. PATENT DOCUMENTS

| | | | | |
|---|---|---|---|---|
| 3,346,704 A | | 10/1967 | Mahoney | |
| 3,557,775 A | | 1/1971 | Mahoney | |
| 3,870,832 A | * | 3/1975 | Fredrickson | 179/107 |
| 5,411,467 A | | 5/1995 | Hortmann et al. | |
| 5,782,744 A | | 7/1998 | Money | |
| 5,814,095 A | * | 9/1998 | Muller et al. | 607/57 |
| 5,859,916 A | | 1/1999 | Ball et al. | |
| 5,881,158 A | * | 3/1999 | Lesinski et al. | 381/174 |
| 5,888,187 A | | 3/1999 | Jaeger et al. | |
| 5,999,632 A | * | 12/1999 | Leysieffer et al. | 381/328 |
| 6,093,144 A | * | 7/2000 | Jaeger et al. | 600/25 |
| 6,243,474 B1 | * | 6/2001 | Tai et al. | 381/174 |

OTHER PUBLICATIONS

Suzuki, Jun–Ichi et al. "Principle, Construction and indication of Middle Ear Implant", Adv. Audiology, vol. 4,pp 15–21 (Kager, Basel 1988).*

Karl–Bernd Huttenbrink, Current Status and Critical Reflections on Implantable Hearing Aids, The American Journal of Otology 20: 409–415, 1999.

Marshall Chasin, "Talk about Good Vibrations! Middle Ear Implants", Hearing Health, vol. 15, No. 3, May/Jun. 1999, 40–41 and 47.

A.E. Deddens et al., "Totally Implantable Hearing Aids; The Effects of Skin Thickness on Microphone Function", American Journal of Otolaryngology, 11:1–4, 1990.

Judith A. Feigin et al., "The Effect of Reference Microphone Placement on Sound Pressure Levels at an Ear Level Hearing Aid Microphone", Ear and Hearing, vol. 11, No. 5, 1990, 321–326.

Tohru Ohno et al., "Structure and Performance of the Main Components", Advances in Audiology, vol. 4, 51–72.

Suzuki, et al., Middle Ear Implant: Implantable Hearing Aid Advances in Audiology, vol. 4, pp. 67–70 and 117–118, Karger, Switzerland.

* cited by examiner

*Primary Examiner*—Jeffrey R. Jastrzab
*Assistant Examiner*—Frances P. Oropeza
(74) *Attorney, Agent, or Firm*—Paul Smith Intellectual Property Law; Paul R. Smith

(57) ABSTRACT

A totally implantable microphone for use with an implanted hearing aid comprises a cylindrical bio-inert housing having a bio-inert metallic membrane at the acoustic sensing end and a bio-inert plate containing electrical lead-throughs at the other end. The cylindrical housing is implanted in the posterior wall of the external auditory canal, with the thin auditory canal skin overlaying the microphone membrane surface. Surface features on the housing ossiointegrate it to the auditory canal bone, and a flange on the housing posterior end prevents post-operative migration into the auditory canal. A support plate beneath the membrane limits inward flexing and increases the signal-to-noise ratio. A protruding rim around the membrane perimeter acts to protect the membrane from rupturing during outward flexure. Lithographically formed wires laminated in a thin inert polymer and connected to the lead-throughs enable the overall length of the encapsulated microphone to be very short.

12 Claims, 7 Drawing Sheets

IMPLANTABLE MICROPHONE FOR USE WITH A HEARING AID OR COCHLEAR PROSTHESIS

FIELD OF THE INVENTION

This invention relates generally to human hearing, and more specifically to the design and surgical insertion and positioning of an implantable microphone.

BACKGROUND OF THE INVENTION

It is estimated that some form of hearing impairment affects over 7% of the U.S. population. Such hearing impairment can be caused by a myriad of factors, for example, trauma, ear infections, congenital factors, ototoxic effects from some antibiotics, and from diseases such as meningitis.

Mild forms of hearing impairment can generally be aided by use of conventional BTE (behind the ear) or CIC (completely in the canal) type hearing aids. Severe hearing impairment may be ameliorated by use of high power conventional hearing aids. For profound hearing loss, the use of cochlear implants may be the only alternative. Other specialized hearing aids, such as bone condition devices, are also available for certain types of hearing impairment.

Conventional hearing aids function by simply amplifying the acoustic signal and transmitting such amplified signal to the ear canal. However, there appears to be a significant social stigma to wearing conventional hearing aids. Also, conventional hearing aids have problems with moisture, audio feedback, ear wax buildup, irritation of the auditory canal skin, amplification of unwanted background noise, and non-linear acoustic distortion, especially at high amplification. Thus, for aesthetic and technical reasons, considerable effort has been directed to developing partially or totally implantable hearing devices. Such devices generally involve one of three basic technologies, namely, vibration of one of the ossicular bones in the middle ear, vibration of the skull bone (i.e. bone anchored devices), or cochlear implants. Prior art devices were usually partially implanted, where part of the electronics, including the microphone, was positioned outside the body near the ear. A review of this technology is presented in "Current Status and Critical Reflections on Implantable Hearing Aids" by K. B. Huttenbrink, Amer. J. of Otology, 20:409–415, 1999. Two of the key technical limitations to achieving totally implanted hearing devices are the existence of a suitable implantable battery and the availability of an implantable microphone. However, some groups have now developed totally implantable hearing devices, some of which are undergoing clinical trials. A brief review of these developments is given by M. Chasin in Hearing Health, Vol. 15, No. 3, May/June 1999, pages 40–41 and 47.

Since totally implantable hearing aids or cochlear prostheses require some form of implantable microphone, there exists prior art dedicated to fabricating a functional implantable microphone. For example Mahoney in U.S. Pat. Nos. 3,346,704 and 3,557,775 teaches a simple silicone rubber tube (approx. 15 mm long) sealed at both ends with a very thin silicone membrane, connected to a microphone at one end. The tube is extended externally from the antrum cell of the mastoid and disposed just beneath the skin, with vibrations picked up through the skin by said tube. T. Ohno et al. pp. 67–68 in Advances in Audiology, Vol. 4, 1988, edited by M. Hoke, describe an electret microphone encased in a stainless steel housing, designed to be located in the wall of the external auditory canal. However, their design of the microphone housing was relatively large and impractical for such implantation. Hortmann et al. in U.S. Pat. No. 5,411,467 teach an implantable microphone connected to a sound conducting tube which distal end is closed by a membrane and projected into the tympanic cavity for acoustic pickup. Money in U.S. Pat. No. 5,782,744 describes a microphone which uses the pressure fluctuations generated within the perilymph fluid of the cochlea scalae as sensing means. Muller et al. in U.S. Pat. No. 5,814,095 describe an electret microphone encased in a titanium housing, which housing has two legs which are oriented at an angle relative to one another, where one leg holds the microphone capsule and covering diaphragm, and the other leg contains the electrical connectors. Leysieffer et al. in U.S. Pat. No. 5,999,632 describe the addition of a projecting elastic flange (on the skin side of the wall of the auditory canal) and another flange near the elbow joint of the two-legged device. Ball et al. in U.S. Pat. No. 5,859,916 describe a two stage implantable microphone where an electret microphone is contained in an internal chamber, which chamber is coupled to another chamber covered with a thin diaphragm. Said diaphragm is protected with a cover containing holes. Lesinski et al. in U.S. Pat. No. 5,881,158 depict a relatively large diameter (10 mm) microphone positioned just below the skin behind the external ear. Their microphone uses a metalized electret (Teflon) film over a partially supported substrate that allows said film to flex due to an acoustic signal. Jaeger et al. in U.S. Pat. No. 5,888,187 teach an implantable two-stage microphone for use by vocally impaired persons. This device is very similar that that shown in U.S. Pat. No. 5,859,916.

Anatomically, there are a variety of possible locations for implanting a microphone. For example, the microphone can be positioned in the bony or cartilaginous ear canal, on the surface of the temporal bone either behind (posterior) or in front (anterior) of the ear, or on either the medial or lateral side of the pinna. Also, a smaller microphone could be inserted into the pinna by attaching it to the cartilage of the pinna or the underlying adjacent bone, with a window made in the pinna cartilage for better acoustic coupling to the microphone input. However, according to the present invention the microphone is anchored (via osseointegration to the bone) in the posterior wall of the bony ear canal. This presents a number of major advantages since sound entering the auditory canal creates a tuned acoustic resonator whereby some key voicing frequencies are enhanced (see for example, A. E. Deddens, et. al., Am. J. Otolaryngol, 11:1–4, 1990; and J. A. Feigin, et. al., Ear and Hearing, Vol. 11, No. 5, 1990). Also, the skin lining the auditory canal is very thin (about 0.1 to 0.2 mm), thus allowing the acoustic signal to be easily transmitted through said skin, thereby inducing relatively unmodified acoustic vibrations in the microphone membrane. These membrane vibrations are sensed by the encapsulated electret microphone.

Other advantages of locating the microphone in posterior wall of the ear canal include: (a) the implantee hears more naturally via the concha and pinna, (b) the bony canal is a good mechanical structure in which to anchor and osseointegrate the microphone housing, thereby minimizing housing migration post surgery and (c) the microphone is safely located and not easily damaged by blows to the side of the head.

It is an object of this invention to provide a totally implantable microphone which provides good acoustic response, is securely retained in the bony ear canal, is adapted to resist high and low ambient pressures, which can be implanted with relative ease and which is of small dimensions to minimize bone dissection and interference with the sigmoid sinus and other adjacent structures.

SUMMARY OF THE INVENTION

The apparatus according to the invention comprises a hermetically sealed small commercial electret type microphone in a biocompatible cylindrical housing, which housing contains novel features adapted for effective, safe and long-term implantation in the posterior wall of the auditory canal.

One feature of the invention is the means by which the thin metallic membrane covering the acoustic input (anterior) end of the microphone housing is protected from rupture during surgical handling, or during subsequent exposure by the implantee to high pressure (i.e. during diving) or to low pressure (i.e. high altitude). Said inventive means has the collateral advantage of greatly increasing the sensitivity of the encapsulated electret microphone to measure the acoustic signal in the air canal. An additional aspect of the invention is the addition of a posteriorly disposed ring-shaped flange on the body of the housing, such flange acting to prevent the microphone housing from migrating anteriorly into the ear canal, thereby rupturing the thin skin lining the wall of the exterior auditory canal or actually extruding.

The invention is a totally implantable microphone, suitable for use with an implanted hearing prosthesis. Said invention comprises a hermetically sealed electret type microphone encapsulated in a cylindrical bio-compatible, preferably metallic, housing, with a flat bio-inert, preferably metallic, base closing one end of said housing, a plurality of electrically insulated lead-throughs disposed through said base, a substantially flat bio-inert metallic membrane closing the other end of said housing, and a support plate positioned below said membrane, such support plate acting to limit the movement of the overlaying membrane during inward flexure of said membrane. In one embodiment of the invention, said membrane contains at least one externally (or internally) protruding ridge near the outside perimeter of said membrane, such ridge acting to provide stress relief for the outward bulging of said membrane during conditions where the pressure outside the housing is lower than the pressure inside the housing.

In a further embodiment of the invention, one or more ridges and or grooves are radially or spirally disposed along the length of the outside wall of said bio-inert housing, so as to assist said housing wall to osseointegrate with the bony wall of the ear canal. Also, a continuous spiral groove (i.e. similar to a screw thread) could be used on the housing outside wall to promote ossiointegration with ear canal bone.

In a yet further embodiment of the invention, lithographically formed wires are laminated in a thin inert polymer, where said wires are connected to the electrical lead-throughs on the flange-side of said housing end, creating a very compact hermetic electrically insulated lead-through configuration, making the overall housing length short, thereby alleviating surgical issues regarding positioning the microphone housing a safe distance from the sigmoid sinus. Said electrically insulated lead-throughs can be achieved by using a base, preferably made of titanium, containing ceramic or bio-inert glass insert(s) acting as electrical insulators, said ceramic (or glass) insert sealed to the titanium base with bio-inert metal (or metals) such as, niobium and/or gold, and, in a further embodiment, the electrical lead-throughs through the glass or ceramic inserts use a bio-inert conductive metal such as gold, tin or an alloy thereof, to create an electrical contact between the microphone and the lithographically formed wires laminated in a thin bio-inert polymer.

Any type of microphone can be encapsulated in the hermetically sealed housing, however, the preferred embodiment is to use a small electret type microphone.

In one aspect of the invention, a totally implantable microphone comprises a microphone encapsulated in a cylindrical bio-inert metallic housing. A bio-inert base is provided at one end of said housing and a membrane closes the other end of the housing. A plurality of electrically insulated lead-throughs are disposed through the base.

In another aspect, a support plate is positioned below the membrane to support the overlaying membrane during inward flexure.

In another aspect, the membrane includes one or more ridges near its outer perimeter to provide stress relief for the outward bulging of the membrane when the pressure outside the housing is lower than the pressure inside the housing.

Preferably one or more ridges and or grooves are radially or spirally disposed along the length of the outside wall of the housing to assist with osseointegration with the bony wall of the ear canal.

In another aspect, a flange is provided on the posterior end of the housing to prevent post-operative migration of the housing into the auditory canal.

In yet another aspect, lithographically formed wires laminated in a thin inert polymer are connected to the electrical lead-throughs on the flange-side of the housing end. This creates a compact hermetic electrically insulated lead-through configuration and makes the overall housing length short.

Preferably the metallic housing and membrane are both made of titanium and the metallic base is comprised of titanium containing one or more ceramic or bio-glass inserts acting as electrical insulators. The insulators are sealed to the titanium base with a low melting point metal or metal alloy.

In yet another of its aspects, the invention is a totally implantable microphone comprising a microphone encapsulated in a cylindrical bio-inert housing, a bio-inert base at one end of the housing and a plurality of electrically insulated lead-throughs disposed through the base. A membrane closes the other end of the housing and a support plate is positioned below the membrane and acts to support the overlaying membrane during inward flexure of the membrane. At least one ridge is provided in the membrane near its outside perimeter to provide stress relief for the outward bulging. A peripheral flange is provided on the posterior end of the housing and lithographically formed wires laminated in a thin inert polymer are connected to the electrical lead-throughs on the flange-side of the housing end.

In yet another aspect the invention comprises the use of a microphone as described above in whereby it is implanted in the wall of the auditory canal such that the membrane underlies the skin of the ear canal and the base is substantially flush with the outside of the wall of the auditory canal.

In another aspect the invention is a microphone assembly for use with an auditory prosthesis comprising a microphone having a cylindrical housing, the microphone being implanted in the wall of the auditory canal such that the membrane underlies the skin of the ear canal and the base is substantially flush with the outside of the wall of the auditory canal. An electronics package is retained in the vicinity of the mastoid cavity, wires are laminated in an inert polymer film and extend from the microphone to the electronics package and a connector line extends between the electronics package and an auditory prosthesis.

Other aspects of the invention will be appreciated by reference to the following descriptions and to the claims.

BRIEF DESCRIPTION OF DRAWINGS

The preferred and alternative embodiments of the invention will be described by reference to the accompanying drawings, where anterior is towards the front, posterior is towards the rear, superior is up, inferior is downwards, and lateral is away from the median of the head.

DESCRIPTION OF THE PREFERRED AND ALTERNATE EMBODIMENTS

The invention includes technical features to safely and successfully anchor said invention to bone and under the skin without subsequent infection, erosion through the skin, or dislocation. Since the microphone itself is not biocompatible, the microphone is hermetically encapsulated with, preferably titanium and ceramic (or glass) containing bio-inert conductive electrical lead-throughs. The overall housing is designed to be small to reduce the amount of bone that needs to be excavated thus reducing the surgical risk. According to the invention the housing is surgically anchored to the bone, and the anterior part of the housing is flush mounted to the surface of the bony auditory canal wall. The length of the microphone housing is kept sufficiently small so that the posteriorly disposed flange (described below) does not to intrude into the sigmoid sinus, an important venous drainage of the brain.

Figure 1:
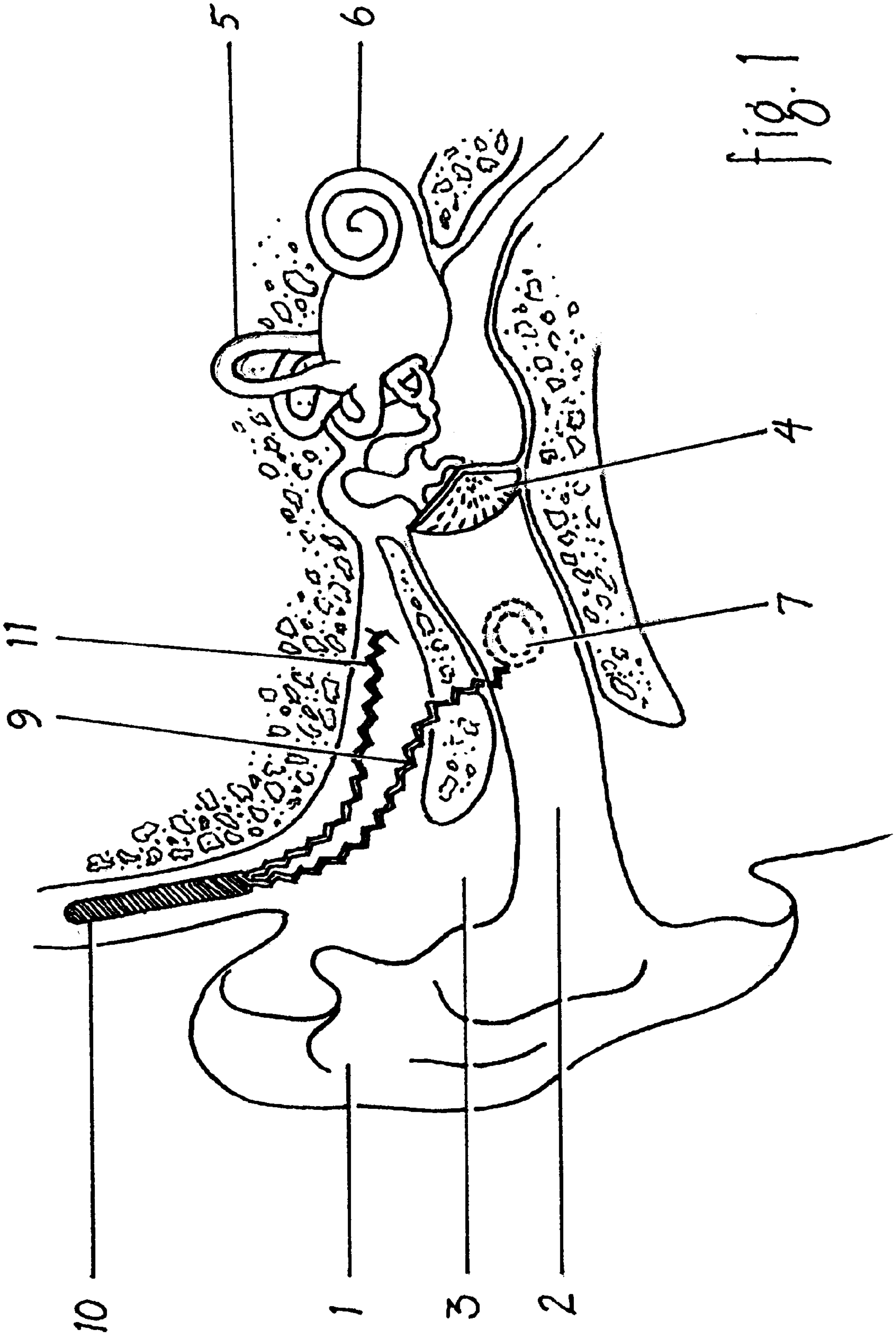
FIG. 1 depicts a coronal diagrammatic view of the pinna, auditory canal, mastoid cavity, tympanic membrane, semicircular canals, and cochlea, with the implanted microphone housing in place.

FIG. 1 depicts a coronal diagrammatic view of the pinna 1, auditory canal 2, mastoid cavity 3, tympanic membrane 4, semicircular canals 5, and cochlea 6, for the right side of the head, with the implanted microphone housing 7 positioned in the posterior wall 8 (shown in FIG. 2) of the auditory canal 2. A similar design is applicable for the left side of the head, however, for simplicity, only the right side is shown. The lithographically formed wires laminated in an inert polymer film connection 9 connect the microphone housing 7 to an electronic package 10. Said polymer film connection 9 is shown corrugated to allow for expansion during device handling and head growth. A corrugated connector line 11 connects said electronic package 10 to an implanted hearing aid or cochlear prosthesis (not shown).

Figure 2:
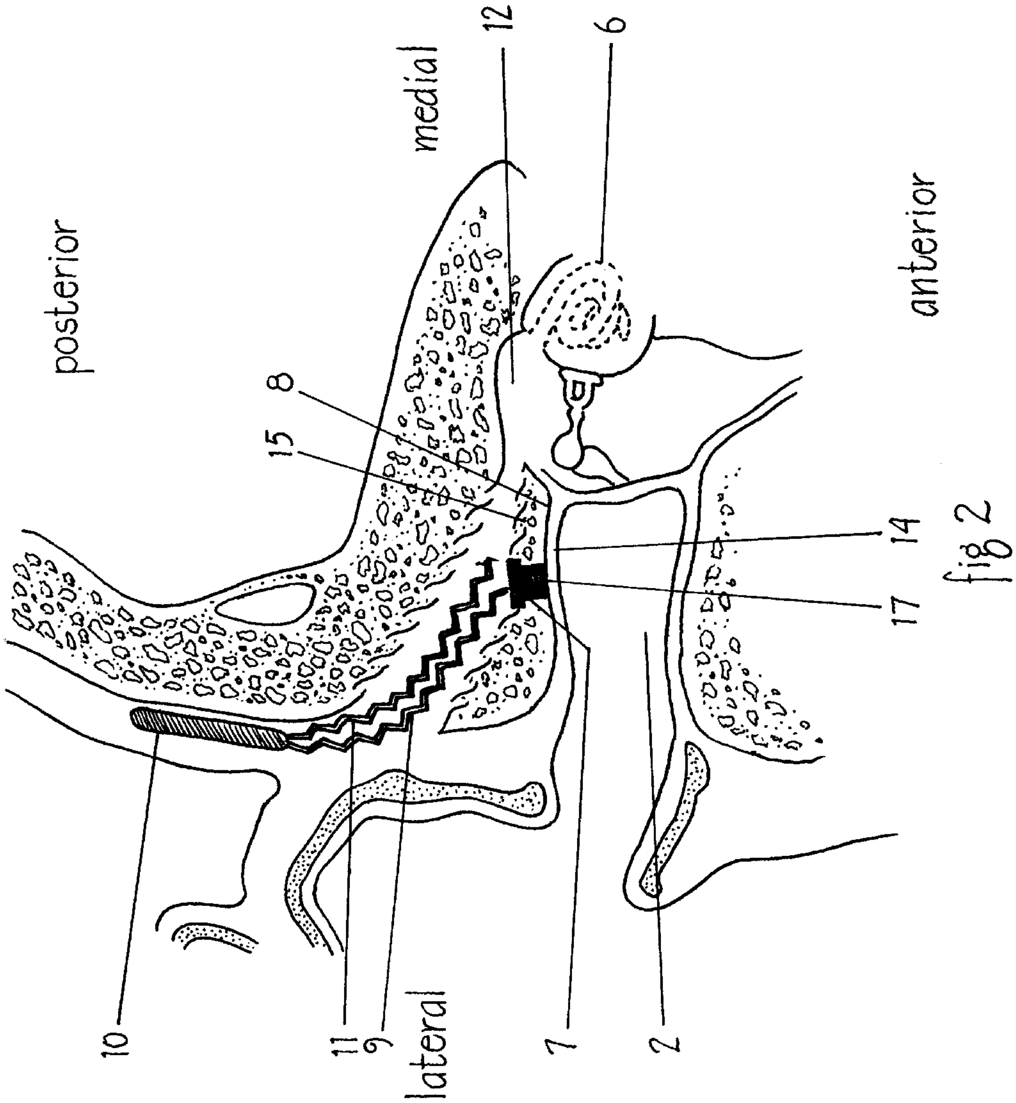
FIG. 2 shows a horizontal cross-sectional view of ear canal, mastoid, middle ear and cochlea, illustrating a surgical approach to gain entry for the microphone housing.

FIG. 2 shows a horizontal cross-sectional view of the auditory canal 2, mastoid cavity 3, middle ear 12 and cochlea 6, illustrating a surgical approach by which a small mastoidectomy cavity is created surgically and the skin 14 of the posterior wall of the external auditory canal is elevated. The bony wall 15 between the mastoid cavity 3 and the auditory canal 2 is thinned down to match the length of the cylindrical microphone housing (less the thickness of the flange), with the bone thickness about 3.5–4 mm (such length being sufficient to obtain osseointegration of the cylinder wall to the bone). The overall length of said housing (including the flange) is about 3–7 mm, preferably about 5 mm. A hole is drilled in the posterior wall about half way between the tympanic ring and the meatus of the external canal. Said hole diameter is made substantially to the diameter of the microphone housing 7 using an appropriately sized drill bit and a custom designed hand tool. The microphone membrane 17, preferably titanium, covering the sound input part of the microphone housing 7, is fitted so as to lie underneath the skin 14, of the posterior wall of the external auditory canal 2. In an alternate embodiment, a protective cap is placed over the titanium membrane 17 during handling to protect it from damage.

Sound entering the implantee's auditory canal 2, will be received by the microphone membrane 17, with the acoustic signal converted to an electrical signal within the microphone, where the electrical signal is then sent to the electronics package 10 for processing.

Figure 3:
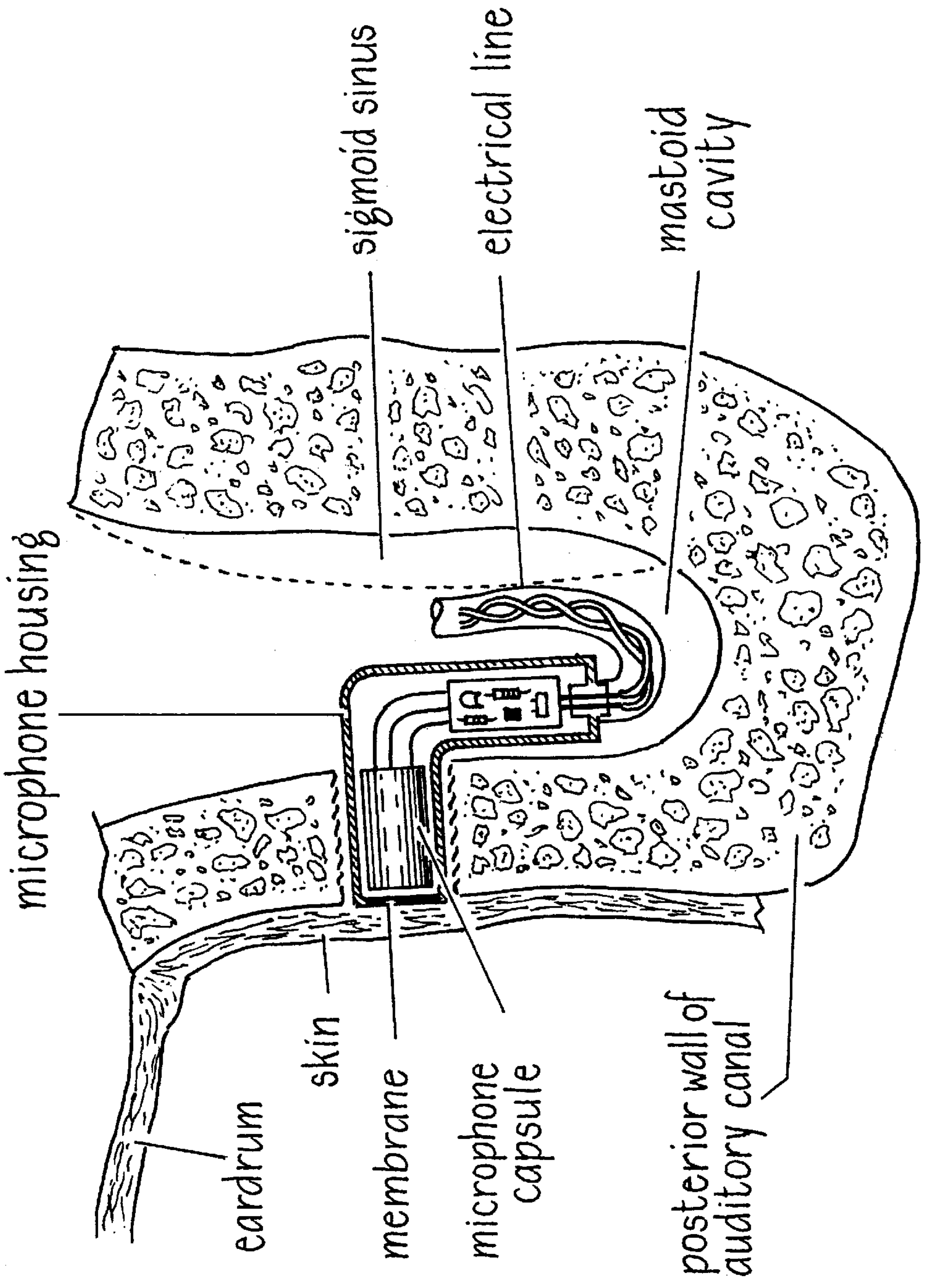
fig. 3 PRIOR ART
FIG. 3 illustrates a sketch of prior art taken from U.S. Pat. No. 5,814,095.

FIG. 3 shows prior art by Muller et al from U.S. Pat. No. 5,814,095 for an implanted microphone. Muller et al. describe an electret type commercial microphone encased in a titanium housing, which housing has two legs which are oriented at an angle relative to one another, where one leg holds the microphone capsule and covering diaphragm, and the other leg contains the electrical connectors. A drawback of said two-legged device is that it is relatively large and awkward, requiring a big excavation of the bone in the posterior wall of the auditory canal, with careful attention required regarding the bony wall of the sigmoid sinus so as to not impact this important venous supply. Another drawback of the two-legged device described by Muller et al. is that this design in inherently mechanically unstable, since the two-legged right angle configuration may twist and thus loosen the device in the bony wall of the canal, which movement can rupture the skin covering the titanium diaphragm, thereby causing the overall device to migrate out of position. Also, the two-legged Muller et al. device does not contain any features to ossiointegrate it to the auditory canal bone, nor to protect the titanium diaphragm from rupture, inwards or outwards. Leysieffer et al. in U.S. Pat. No. 5,999,632 add a flange to one leg of the two-legged device in the Muller et al. '095' Patent. Additionally, they add a projecting elastic flange to the membrane side of the device, such elastic flange designed to be placed against the side of the wall facing the skin of the auditory canal. However, the addition of said elastic flange creates two distinct problems. Firstly, the addition of the flange protrudes slightly into the ear canal, forcing the very thin skin lining the ear canal, which is about 0.1–0.2 mm thick, to grow over and around such a protrusion, creating the issue of possible erosion due to the interruption of the smooth growth of the auditory skin, and/or skin erosion due to cleaning or the presence of a foreign object in the ear canal. Secondly, the distance between the elastic flange and the flange created by the one-leg of the device (referred to as distance 'a' in their FIG. 4, or in FIG. 8) is very thin, creating a requirement for highly fragile and accurate dimensional drilling of auditory bone to position said device. Such accurate drilling is impractical in view of the cellular nature of the bone marrow and air cells. Said method is also conducive to possible failure due to loosening of the microphone over time since their device does not use the principle of metal to bone osseointegration.

Figure 4:
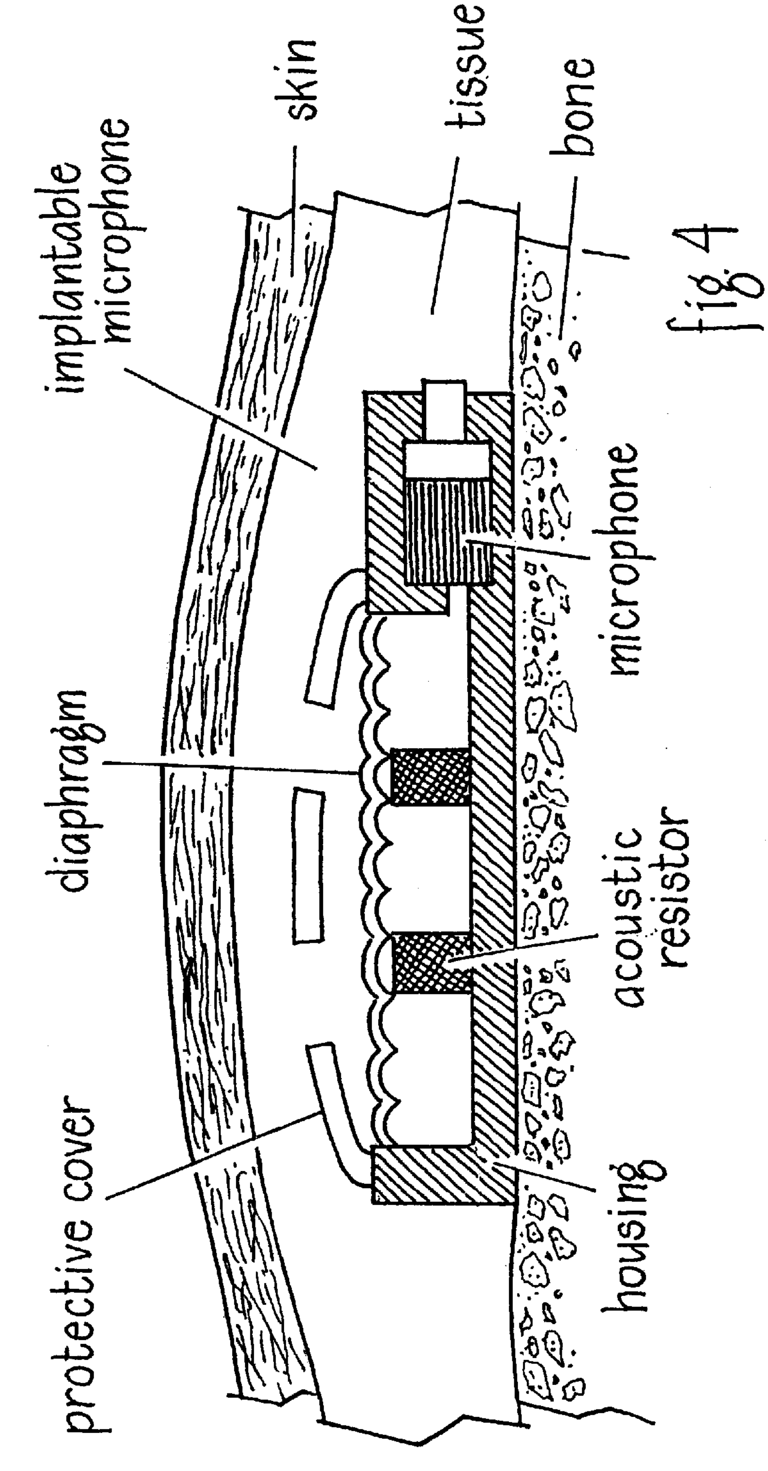
fig 4 PRIOR ART
FIG. 4 illustrates a sketch of prior art taken from U.S. Pat. No. 5,859,916.

FIG. 4 illustrates prior art by Ball et al. in U.S. Pat. No. 5,859,916. They describe a two stage implantable microphone where an electret microphone is contained in an internal chamber, which chamber is coupled to another chamber covered with a thin diaphragm. Said diaphragm is protected from above with a cover containing holes, and by an acoustic resistor element mounted beneath said diaphragm. This prior art has a major limitation in that the microphone is designed to be implanted below the skin behind the outer ear or concha, which location does not make use of the natural acoustic resonance features of the auditory canal. Additionally, such location requires that the diameter of the device be relatively large so as to overcome the acoustic attenuation of the overlaying skin, such overlaying skin being much thicker than the very thin skin lining the auditory canal. Additionally, such a location renders this device very prone to injury.

Figure 5:
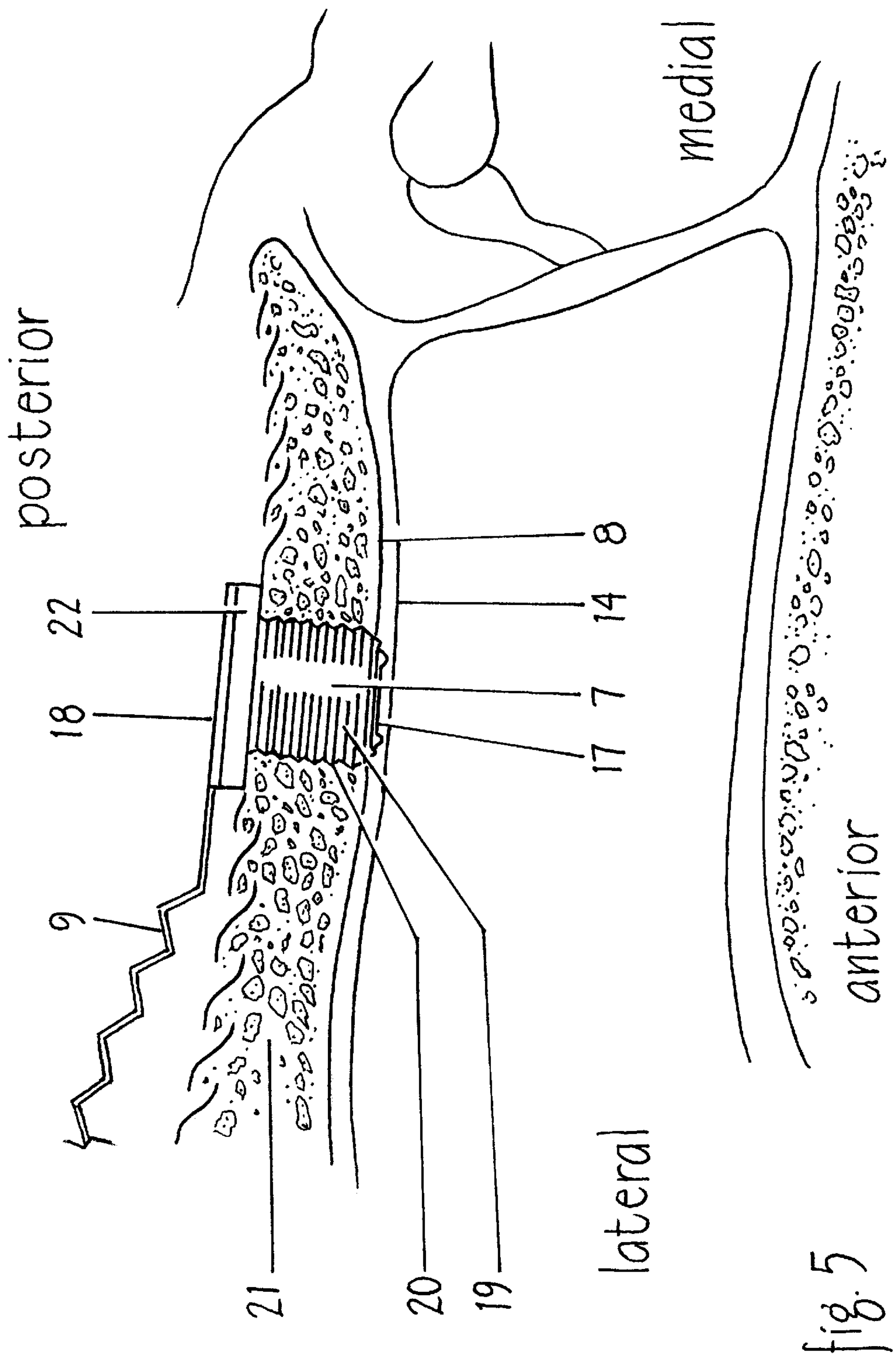
FIG. 5 shows a cross-sectional enlarged sketch of the invention osseointegrated into the bone of the auditory canal.

FIG. 5 shows a sketch of the invention 18 in place. The cylindrical wall 19 of the microphone housing 7 contains "notches", "circular grooves" or a "grooved spiral" 20 to aid in osseointegrating the cylindrical wall 19 to the auditory canal bone 21. This novel design allows for a tight, well-anchored and safe positioning of the microphone. A posterior disposed flange 22 on the microphone housing 7 acts to aid the surgeon in implanting the invention 18 to position the microphone membrane 17 flush to posterior wall 8. Said flange 22 also acts to prevent the invention 18 from migrating into the auditory canal 2 before osseointegration has occurred. The thin migratory skin 14 of the auditory canal 2 overlays the microphone membrane surface 17, which skin 14 seals the invention 18 from direct contact with air and materials in the auditory canal 2.

Figure 6:
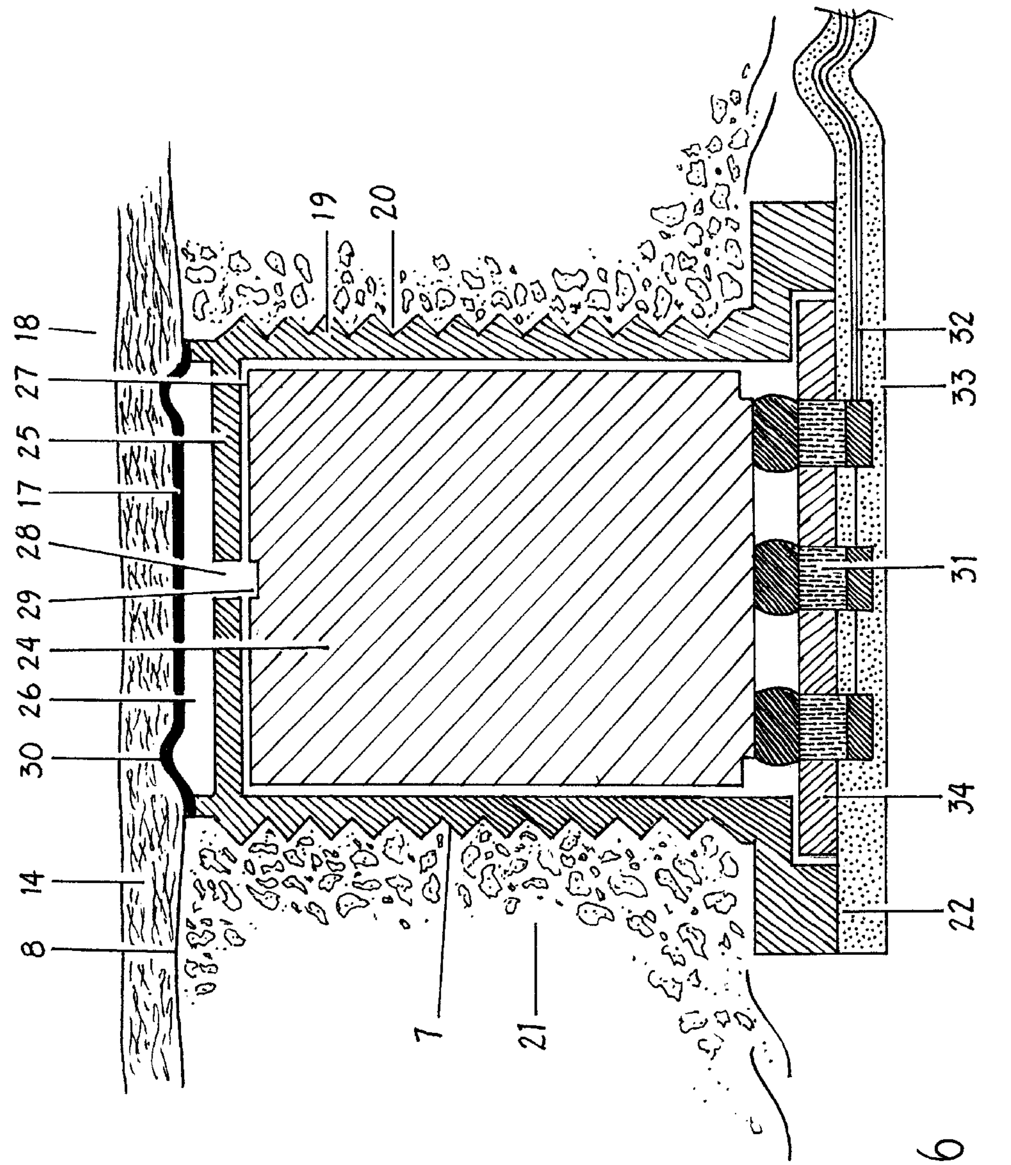
FIG. 6 is a cross-sectional drawing of the microphone encapsulated in a hermetically sealed housing.

FIG. 6 is a cross-sectional drawing of the invention 18 with the microphone 24 encapsulated in cylindrical housing 7. The microphone membrane 17, preferably made of titanium, must be sufficiently thin to transmit the acoustic signal in the auditory canal 2 to the air cavity 26 and microphone 24, to achieve an acceptable signal-to-noise ratio. The thickness of the membrane 17 can be about 5–15 $\mu$m, preferably about 8–10 $\mu$m. Other biocompatible metals, such as iridium or tantalum can also be used for the membrane.

The base plate 34 contains electrical lead-throughs 31 comprised of ceramic (or bio-inert glass) insert(s) 35 acting as electrical insulators. Said ceramic (or glass) inserts 35 are sealed to the, preferably titanium, base with bio-inert metal (or metals) such as, niobium and/or gold. In a further embodiment, the electrical lead-throughs 31 through the ceramic (or glass) inserts 35 use a bio-inert conductive metal such as gold, tin or an alloy thereof, to create an electrical contact between the microphone and the lithographically formed wires 32 laminated in a thin bio-inert polymer 33.

Since the auditory canal 2 (not shown in FIG. 6) is generally about 10 mm diameter, the diameter of the microphone housing must be significantly smaller than 10 mm to achieve a substantially flush positioning of the microphone membrane 17 to the surface of posterior wall 8 in the auditory canal. From a surgical and technical perspective, the diameter of the microphone housing 7 can be about 3 mm to 5 mm, preferably about 4 mm.

Since the microphone membrane 17 is relatively thin, and fragile, a support plate 25 is positioned below, and very close to, said membrane 17. The top surface 27 of microphone 24 is sealed to the underside of the support plate 25. The air cavity 26 that separates the membrane 17 and support plate 25 is about 5–500 $\mu$m, preferably about 25–100 $\mu$m, so that a force causing the membrane 17 to flex inwards is stopped by the support plate 25, thus preventing the membrane 17 from possible rupture. The support plate 25 also contains a small hole 28, about 50–500 $\mu$m in diameter, such hole 28 acting to transmit the pressure changes in air cavity 26 to microphone 24 whose inlet 29 (not shown in FIG. 6) is disposed below the support plate 25. The small air cavity 26 also acts to maximize the pressure changes occurring in said air cavity due to slight (acoustically induced) movements of the membrane 17, thus increasing the sensitivity of the microphone to the acoustic signal in the auditory canal.

The outer perimeter of the microphone membrane 17, contains one (or more) protruding ridges 30 to protect the membrane 17 from rupturing during outward bulging of the membrane 17 due to a lower pressure outside the membrane 17 compared to the fixed air pressure inside the air cavity 26. Said ridge (or ridges) 30 act to reduce the tensile force on the thin membrane 17 during an outward bulge of said membrane.

The use of "notches", "grooves" or "threads" 20 on the outside surface of the housing cylinder 19, preferably made of titanium, act to help osseointegrate the housing wall 19 to the bony wall of the auditory canal 21. Those skilled in the art will appreciate that the use of notches, grooves or threads is a well-known and established technology for anchoring dental prosthesis to bone and also for holding bone-anchored (percutaneous type) hearing aids to the skull. However, no application of this technology is evident for anchoring a microphone housing in the bony wall of the ear canal.

The posterior end of the housing has a flange 22, preferably made of titanium, surrounding a ceramic (or bio-glass) insert, said insert containing hermetically sealed electrical lead-throughs 31, which lead-throughs are comprised of platinum, gold or any biocompatible conducting metal. Lithographically formed wires 32, preferably in platinum and/or gold, laminated in a thin 25–250 $\mu$m inert polymer 33, such as a fluorocarbon, preferably FEP, are aligned with said electrical lead-throughs 31. The electrical connection between said electrical lead-throughs 31 and the lithographic wires 32 is formed using a low temperature melting point biocompatible metal such as tin, indium or alloys such as gold/indium or tin/silver. Such design creates a low profile hermetic electrical lead-through at the posterior end of the microphone housing, which design reduces the size of the surgical excavation necessary to position said housing in the bony wall of the auditory canal.

Figure 7:
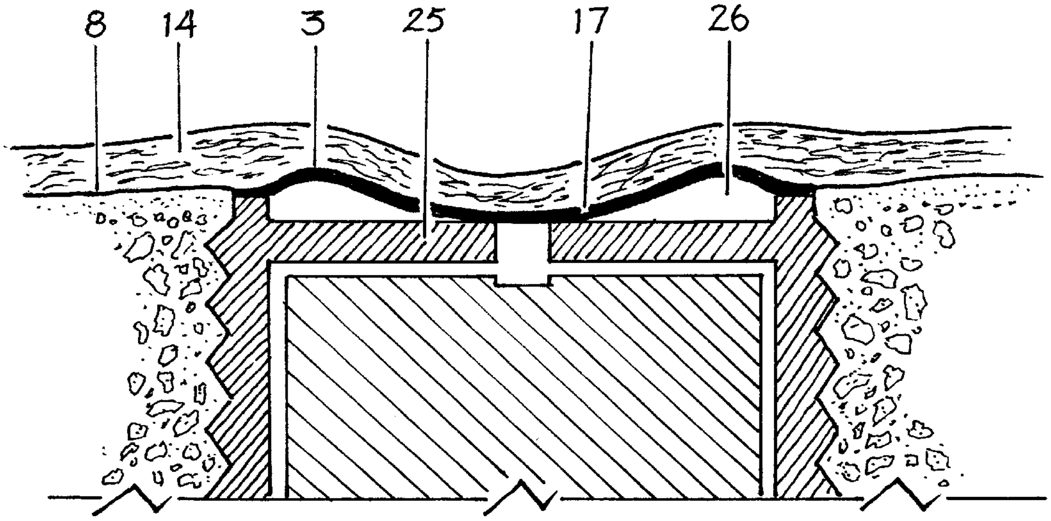
FIG. 7 shows the (acoustic sensing) microphone membrane being flexed inwards.

FIG. 7 shows the (acoustic sensing) microphone membrane 17 being flexed inwards, with auditory canal skin 14 covering said microphone membrane 17. The ridge (or ridges) 30 act to minimize the tensile force on the thin microphone membrane 17 during inward flexure. The support plate 25 prevents the said membrane 17 from flexing further, and possibly rupturing. The extent of maximum flexure of membrane 17 is designed to remain within the elastic portion of the stress-strain curve of the membrane material.

Figure 8:
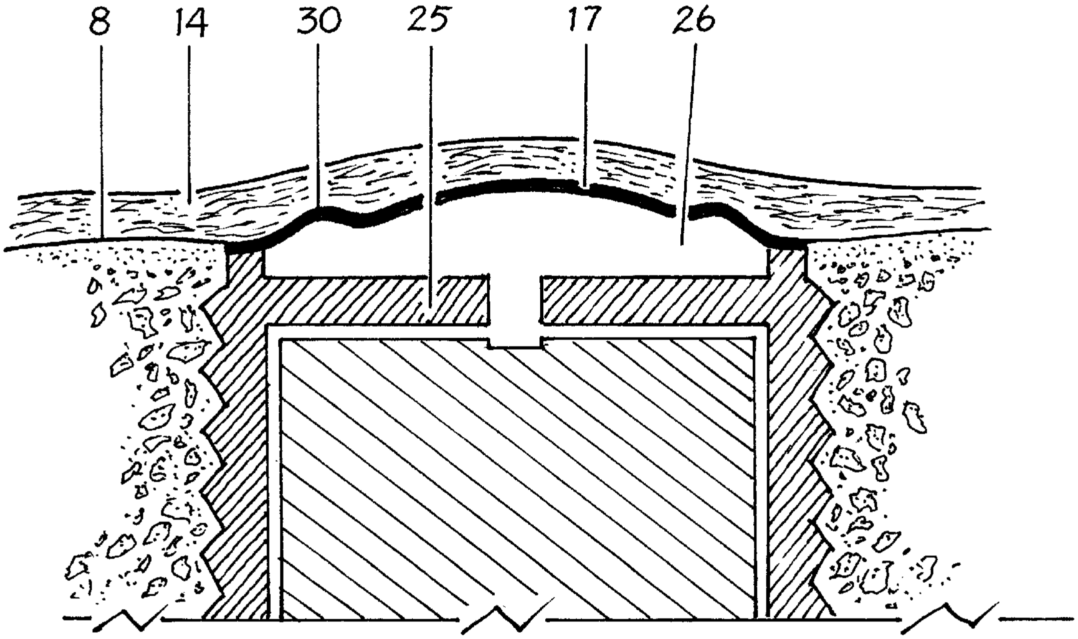
FIG. 8 shows the (acoustic sensing) microphone membrane being flexed outwards.

FIG. 8 shows the acoustic sensing microphone membrane being flexed outwards. The ridge (or ridges) 30 act to minimize the tensile force on the thin microphone membrane 17 during outward flexure. Such outward flexure can occur if the ambient pressure in the ear canal is reduced, by for example, the implantee being at high altitude. The extent of maximum outward flexure of membrane 17 is designed to remain within the elastic portion of the stress-strain curve of the membrane material.

The above descriptions have been intended to illustrate the preferred and alternative embodiments of the invention. It will be appreciated that modifications and adaptations to such embodiments may be practiced without departing from the scope of the invention, such scope being most properly defined by reference to this specification as a whole and to the following claims.

What is claimed is:

1. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone;

a plate positioned between said membrane and said microphone and being spaced from said membrane, said plate acting to limit inward flexure of said membrane; and a flange on said one end of said housing to prevent post-operative migration of the housing into the auditory canal of a patient in which said assembly may be implanted.

2. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone; and a flange on said one end of said housing to prevent post-operative migration of the housing into the auditory canal of a patient in which said assembly may be implanted, and lithographically formed wires laminated in a thin inert polymer, said wires being connected to the electrical lead-throughs on the flange-side of said housing, creating a compact hermetic electrically insulated lead-through configuration and making said housing short.

3. The assembly of claim 2 where said base is comprised of titanium containing one or more ceramic or bio-glass inserts acting as electrical insulators, said insulators sealed to the titanium base with a low melting point metal or metal alloy.

4. The assembly of claim 3 where the low temperature metal or metal alloy is indium, tin or gold/tin.

5. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone;

a plate positioned between said membrane and said microphone and being spaced from said membrane, said plate acting to limit inward flexure of said membrane; and a flange on said one end of said housing to prevent post-operative migration of the housing into the auditory canal of a patient in which said assembly may be implanted, and lithographically formed wires laminated in a thin inert polymer, said wires being connected to the electrical lead-throughs on the flange-side of said housing, creating a compact hermetic electrically insulated lead-through configuration and making said housing short.

6. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone; and at least one ridge in said membrane near an outside perimeter of said membrane, such ridge acting to provide stress relief for the outward bulging of said membrane during conditions where the pressure outside the housing is lower than the pressure inside the housing; and a flange on said one end of said housing to prevent post-operative migration of the housing into the auditory canal of a patient in which said assembly may be implanted, and lithographically formed wires laminated in a thin inert polymer, said wires being connected to the electrical lead-throughs on the flange-side of said one end, creating a compact hermetic electrically insulated lead-through configuration and making said housing short.

7. A totally implantable microphone assembly comprising:

a microphone encapsulated in a cylindrical bio-inert housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone;

a plate positioned below said membrane, said plate acting to limit inward flexure of said membrane;

at least one ridge in said membrane near an outside perimeter of said membrane, said ridge acting to provide stress relief for the outward bulging of said membrane;

a peripheral flange on said one end of said housing; and, lithographically formed wires laminated in a thin inert polymer, said wires being connected to the electrical lead-throughs on the flange-side of said one end.

8. The assembly of claim 7 wherein said housing is between about 3 and 7 mm in length.

9. The assembly of claim 7 wherein said membrane has a thickness between about 5 and 15 $\mu$m.

10. The use of the assembly of claim 7 wherein said microphone is adapted to be implanted in the bone of the wall of the auditory canal of a patient in which said assembly may be implanted such that said membrane underlies the skin of the ear canal of said patient and said base is substantially flush with the interior wall of said auditory canal.

11. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone; and a flange on said one end of said housing to prevent post-operative migration of the housing into the auditory canal of a patient in which said assembly may be implanted.

12. A totally implantable microphone assembly comprising:

a microphone encapsulated in a cylindrical bio-inert metallic housing;

a bio-inert base at one end of said housing;

a plurality of electrically insulated lead-throughs disposed through said base;

a substantially unsupported membrane sealing the other end of said housing so as to enclose a volume of gas within said housing, said gas acting as a transmission medium between said membrane and said microphone;

at least one ridge in said membrane near an outside perimeter of said membrane, such ridge acting to provide stress relief for the outward bulging of said membrane during conditions where the pressure outside the housing is lower than the pressure inside the housing; and a flange on said one end of said housing to prevent post-operative migration of the housing into the auditory canal of a patient in which said assembly may be implanted.

* * * * *